(12) United States Patent
Beaty

(10) Patent No.: US 7,550,091 B2
(45) Date of Patent: *Jun. 23, 2009

(54) IMPLANT SURFACE PREPARATION

(75) Inventor: Keith D. Beaty, Jupiter, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/070,487

(22) Filed: Feb. 19, 2008

(65) Prior Publication Data

US 2008/0160168 A1  Jul. 3, 2008

Related U.S. Application Data

(63) Continuation of application No. 11/651,115, filed on Jan. 9, 2007, which is a continuation of application No. 11/172,775, filed on Jul. 1, 2005, now Pat. No. 7,169,317, which is a continuation of application No. 10/701,855, filed on Nov. 5, 2003, now Pat. No. 6,969,474, which is a continuation of application No. 09/777,335, filed on Feb. 6, 2001, now Pat. No. 6,652,765, which is a continuation of application No. 09/259,432, filed on Mar. 1, 1999, now Pat. No. 6,491,723, which is a continuation of application No. 08/607,903, filed on Feb. 27, 1996, now Pat. No. 5,876,453, which is a continuation-in-part of application No. 08/351,214, filed on Nov. 30, 1994, now abandoned.

(51) Int. Cl.
*B44C 1/22* (2006.01)
*C03C 25/68* (2006.01)
*C23F 1/00* (2006.01)
*C25F 3/00* (2006.01)

(52) U.S. Cl. ..................... 216/109; 427/2.26

(58) Field of Classification Search ............... 623/901, 623/16.11, 20.17, 23.29, 23.5, 23.55; 216/109; 427/2.24, 2.26; 433/201.1, 174

See application file for complete search history.

(56) References Cited

U.S. PATENT DOCUMENTS 3,022,783 A  2/1962  Tucker, Jr.

(Continued)

FOREIGN PATENT DOCUMENTS

AT  328 067  5/1975

(Continued)

OTHER PUBLICATIONS

A histomorphometric and removal torque study of screw-shaped titanium implants with three different surface topographies (Ref. D33), 1995.

(Continued)

*Primary Examiner*—Roberts Culbert
(74) *Attorney, Agent, or Firm*—Nixon Peabody LLP

(57) ABSTRACT

The surface of a device that is surgically implantable in living bone is prepared. The device is made of titanium with a native oxide layer on the surface. The method of preparation comprises the steps of removing the native oxide layer from the surface of the device and performing further treatment of the surface substantially in the absence of unreacted oxygen.

35 Claims, 6 Drawing Sheets

U.S. PATENT DOCUMENTS

| | | |
|---|---|---|
| 3,605,123 A | 9/1971 | Hahn |
| 3,767,437 A | 10/1973 | Cruz, Jr. |
| 3,790,507 A | 2/1974 | Hodosh |
| 3,855,638 A | 12/1974 | Pilliar |
| 3,919,723 A | 11/1975 | Heimke et al. |
| 3,986,212 A | 10/1976 | Sauer |
| 3,987,499 A | 10/1976 | Scharbach et al. |
| 4,011,602 A | 3/1977 | Rybicki et al. |
| 4,051,598 A | 10/1977 | Sneer |
| 4,145,764 A | 3/1979 | Suzuki et al. |
| 4,146,936 A | 4/1979 | Aoyage et al. |
| 4,180,910 A | 1/1980 | Straumann et al. |
| 4,195,409 A | 4/1980 | Child |
| 4,199,864 A | 4/1980 | Ashman |
| 4,223,412 A | 9/1980 | Aoyagi et al. |
| 4,261,350 A | 4/1981 | Branemark et al. |
| 4,330,891 A | 5/1982 | Branemark et al. |
| 4,336,618 A | 6/1982 | Raab |
| 4,366,183 A | 12/1982 | Ghommidh et al. |
| 4,406,761 A | 9/1983 | Shimogori et al. |
| 4,530,116 A | 7/1985 | Frey |
| 4,547,157 A | 10/1985 | Driskell |
| 4,547,327 A | 10/1985 | Bruins et al. |
| 4,608,052 A | 8/1986 | Van Kampen et al. |
| 4,629,464 A | 12/1986 | Takata et al. |
| 4,654,314 A | 3/1987 | Takagi et al. |
| 4,687,675 A | 8/1987 | Nakano et al. |
| 4,693,986 A | 9/1987 | Vit et al. |
| 4,702,930 A | 10/1987 | Heide et al. |
| 4,704,126 A | 11/1987 | Baswell et al. |
| 4,722,688 A | 2/1988 | Lonca |
| 4,746,532 A | 5/1988 | Suzuki et al. |
| 4,818,559 A | 4/1989 | Hama et al. |
| 4,826,434 A | 5/1989 | Krueger |
| 4,839,215 A | 6/1989 | Starling |
| 4,861,733 A | 8/1989 | White |
| 4,865,603 A | 9/1989 | Noiles |
| 4,871,578 A | 10/1989 | Adam et al. |
| 4,874,434 A | 10/1989 | Riggs, Jr. |
| 4,878,914 A | 11/1989 | Miwa et al. |
| 4,882,196 A | 11/1989 | Shimamune et al. |
| 4,908,030 A | 3/1990 | Linkow et al. |
| 4,911,953 A | 3/1990 | Hosonuma et al. |
| 4,919,751 A | 4/1990 | Sumita et al. |
| 4,932,868 A | 6/1990 | Linkow et al. |
| 4,938,938 A | 7/1990 | Ewers et al. |
| 4,944,754 A | 7/1990 | Linkow et al. |
| 4,960,646 A | 10/1990 | Shimamune et al. |
| 4,963,145 A | 10/1990 | Takagi et al. |
| 4,969,906 A | 11/1990 | Kronman |
| 4,988,299 A | 1/1991 | Branemark |
| 5,000,685 A | 3/1991 | Brajnovic |
| 5,030,096 A | 7/1991 | Hurson et al. |
| 5,032,552 A | 7/1991 | Nonami et al. |
| 5,034,352 A | 7/1991 | Vit et al. |
| 5,039,546 A | 8/1991 | Chung et al. |
| 5,071,351 A | 12/1991 | Green et al. |
| 5,108,399 A | 4/1992 | Eitenmuller et al. |
| 5,141,576 A | 8/1992 | Shimamune et al. |
| 5,180,564 A | 1/1993 | Wahl et al. |
| 5,188,800 A | 2/1993 | Green et al. |
| 5,190,795 A | 3/1993 | Culler |
| 5,195,891 A | 3/1993 | Sulc |
| 5,199,873 A | 4/1993 | Schulte et al. |
| 5,205,745 A | 4/1993 | Kamiya |
| 5,205,921 A | 4/1993 | Shirkanzadeh |
| 5,219,361 A | 6/1993 | von Recum et al. |
| 5,222,983 A | 6/1993 | Schmitz et al. |
| 5,242,706 A | 9/1993 | Cotell et al. |
| 5,258,030 A | 11/1993 | Wolfarth et al. |
| 5,263,986 A | 11/1993 | Noiles et al. |
| 5,279,831 A | 1/1994 | Constantz et al. |
| 5,297,963 A | 3/1994 | Dafatry |
| 5,306,305 A | 4/1994 | Lee |
| 5,310,464 A | 5/1994 | Redepenning |
| 5,316,476 A | 5/1994 | Krauser |
| 5,316,477 A | 5/1994 | Calderon |
| 5,324,199 A | 6/1994 | Branemark |
| 5,344,425 A | 9/1994 | Sawyer |
| 5,344,457 A | 9/1994 | Pilliar |
| 5,360,448 A | 11/1994 | Thramann |
| 5,362,237 A | 11/1994 | Chalifoux |
| 5,366,374 A | 11/1994 | Vlassis |
| 5,368,480 A | 11/1994 | Balfour et al. |
| 5,368,483 A | 11/1994 | Sutter et al. |
| 5,399,090 A | 3/1995 | Padros-Fradera |
| 5,405,436 A | 4/1995 | Maurer et al. |
| 5,427,754 A | 6/1995 | Nagata et al. |
| 5,433,606 A | 7/1995 | Niznick et al. |
| 5,441,536 A | 8/1995 | Aoki et al. |
| 5,456,723 A | 10/1995 | Steinemann et al. |
| 5,472,734 A | 12/1995 | Perrotta et al. |
| 5,478,237 A | 12/1995 | Ishizaswa |
| 5,484,286 A | 1/1996 | Hansson |
| 5,489,210 A | 2/1996 | Hanosh |
| 5,496,399 A | 3/1996 | Ison et al. |
| 5,503,558 A | 4/1996 | Clokie |
| 5,543,019 A | 8/1996 | Lee et al. |
| 5,564,923 A | 10/1996 | Grassi et al. |
| 5,571,017 A | 11/1996 | Niznick |
| 5,571,188 A | 11/1996 | Ellingsen et al. |
| 5,573,401 A | 11/1996 | Davidson et al. |
| 5,588,838 A | 12/1996 | Hansson et al. |
| 5,591,029 A | 1/1997 | Zuest |
| 5,603,338 A | 2/1997 | Beaty |
| 5,639,237 A | 6/1997 | Fontenot |
| 5,863,201 A | 1/1999 | Lazzara et al. |
| 5,876,453 A | 3/1999 | Beaty |
| 5,989,027 A | 11/1999 | Wagner et al. |
| 6,069,295 A | 5/2000 | Leitao |
| 6,491,723 B1 | 12/2002 | Beaty ...................... 623/11.11 |
| 6,652,765 B1 | 11/2003 | Beaty |

FOREIGN PATENT DOCUMENTS

| | | | |
|---|---|---|---|
| CA | 926552 | 5/1973 | ........................ 3/1 |
| CH | 679117 A5 | 12/1991 | |
| DE | 2 313 678 | 10/1974 | |
| DE | 27 17 615 A1 | 10/1978 | |
| EP | 202031 A2 | 11/1986 | |
| EP | 212929 A2 | 3/1987 | |
| EP | 0213836 | 11/1987 | |
| EP | 0409810 | 1/1991 | |
| EP | 455929 A1 | 1/1991 | |
| EP | 606566 A1 | 7/1994 | |
| FR | 2 289 160 | 10/1974 | |
| FR | 2 421 595 | 11/1979 | |
| GB | 834256 | 5/1960 | |
| GB | 2045083 A | 1/1984 | |
| GB | 2252501 A | 8/1992 | |
| JP | 1148254 | 6/1989 | |
| JP | 3146679 A2 | 6/1991 | |
| SE | 332 486 | 11/1971 | |
| WO | WO 92/05745 | 4/1992 | |
| WO | WO 94/13334 A | 6/1994 | |

OTHER PUBLICATIONS

Adhesion of Bone to Titanium (Ref. 27), 1996.
Albrektsson, T., P.I. Branemark, H.A. Hansson & J. Lindstrom, "Osseointegrated Titanium Implants," 1991.
An animal study of c.p. titanium screws with different surface topographies (Ref. D 32), 1995.
ASTM Designation F 86-84, "*Standard Practice for Surface Preparation and Marking of Metallic Surgical Implants*", 1996.

Baier, R. E., et al., "*Surface Energetics And Biological Adhesion*," International Symposium on Physicochemical Aspects of Polymer Surfaces, vol. 2, pp. 895-909, 1981.

Baier, R.E; A.E. Meyer "*Implant Surface Preparation*," International Journal of Oral & Maxillofacial Implants, vol. 3, 9-20, 1988.

Binon, P. "*Evaluation of Machining Accuracy and Consistency of Selected Implants, Standard Abutments, and Laboratory Analogs*," The International Journal of Prosthodontics, vol. 8, 162-178, 1995.

Bio Materials 1996 vol. 17, No. 6 pp. 605-616 "Bone response to surface-modified titanium implants: studies on the early tissue response to machined and electropolished implants with different oxide thicknesses", Larsson et al.

Bio Materials 1994 vol. 15, No. 13, pp. 1062-1074 "Bone response to surface modified titanium implants: studies on electropolished implants with different oxide thicknesses and morphology", Larsson et al.

Buser et al., "Interface Shear Strength of Titanium Implants With a Sandblasted and Acid-Etched Surface: A Biomechanical Study in the Maxilla of Miniature Pigs," *J Biomed Mater Res*, 45 (1999), pp. 75-83.

Boyan et al., "Titanium Surface Roughness Alters Responsiveness of MG63 Osteoblast-Like Cells to $1\alpha,25\text{-}(OH)_2D_3$," *J Miomed Mater Res*, 39 (1998), pp. 77-85.

Bowers, K.; Keller, J.; Randolph, B.; Wick, D.; Michaels, C. "*Optimization of Surface Micromorphology for Enhanced Osteoblast Responses In Vitro*" International Journal of Oral & Maxillofacial Implants. vol. 7 No. 3, pp. 302-310, 1992.

Branemark, P.I.; et al, *Osseointegrated implants in the Treatment of the Edentulous Jaw Experience from a 10-year period*, Stockholm, Almqvist & Wiksell International, 1977.

Per-Ingvar Branemark, M.D., Ph.D., "Tissue-Integrated Prostheses" (Ref. 43), 1985.

Buser, D., et al., "*Influence Of Surface Characteristics On Bone Integration Of Titanium Implants, A Histomorphometric Study In Miniature Pigs*," Journal of Biomedical Materials Research, vol. 25, pp. 889-902 (1991).

Daniel Buser, DDS, et al., "Removal Torque Values of Titanium Implants in the Maxilla of Miniature Pigs", pp. 611-619, 1998.

Carlsson L.; T. Rostlund; B. Albrektsson; T. Albrektsson "*Removal Torques for Polished and Rough Titanium Implants*," International Journal of Oral & Maxillofacial Implants, vol. 3, 21-24, 1988.

Cochran et al., "Bone Response to Unloaded and Loaded Titanium Implants With a Sandblasted and Acid-Etched Surface: A Histometric Study in the Canine Mandible," *J Biomed Mater Res*, 40 (1998), pp. 1-11.

Cochran et al., "Evaluation of an Endosseous Titanium Implants With a Sandblasted and Acid-Etched Surface in the Canine Mandible: Radiographic Results," *Clinical Oral Implants Research* 1996: 7: 240-252.

Cook, S.; F. Georgette; H. Skinner; R. Haddad, Jr. "*Fatigue properties of carbon- and porous-coated Ti-6Al-4V alloy*," Journal of Biomedical Materials Research, vol. 18, 497-512, 1984.

Stephen D. Cook, Ph.D. et al., "Interface Mechanics and Histology of Titanium and Hydroxylapatite-Coated Titanium for Dental Implant Applications" (Ref. 47), 1987.

Curtis, A. S. G., et al., "The Effects Of Topographic And Mechanical Properties Of Materials On Cell Behavior," *Critical Reviews in Biocompatibility*, vol. 5, Issue 4, pp. 343-362 (1990).

Das Prinzip der neuen Ledermann-Schraube (German Reference D3), 1988.

de Groot, K., et al., "*Plasma Sprayed Coatings Of Hydroxylapatite*," Journal of Biomedical Materials Research, vol. 21, pp. 1375-1381 (1987).

C. de Putter et al., Implant Materials in Biofunction, "Removal Forces For Osseointegrated Titanium Implants" (Ref. 31), 1988.

Declaration of Prabhu Gubbi presenting information on the surfaces of 61 implants (Nov. 2, 2001).

Denar Introduces Steri-Oss: The First Complete Oral Rehabilitation Implant System.

"Design and Surface Characteristics of 13 Commercially Available Oral Implant Systems," *Int. J. Oral Maxillofactial Implants*, 1993, 8:622-633.

Eberhardt, A., et al., "*Effects Of Precoating Surface Treatments On Fatigue Of Ti-6Al-4V*," Journal of Applied Biomaterials, vol. 6, pp. 171-174 (1995).

Effect of a Blycoprotein Monomolecular Layer on the Integration of Titanium Implants in Bone (Ref. D48), 1985.

Gomez-Roman, German, et al., "The Frialit-2 Implant System: Five-Year Clinical Experience In Single-Tooth And Immediately Postextraction Applications," The International Journal of Oral & Maxillofacial Implants, vol. 12, No. 3, pp. 299-309 (1997).

Gotfredsen, K., et al., "Histomorphometric And Removal Torque Analysis for $TiO_2$-Blasted Titanium Implants" Clinical Oral Impl. Res., Feb. 6, 1992, pp. 77-84.

Edited by G. Heimke, U.Soltesz and A.J.C. Lee, "The Influence of Various Titanium Surfaces on the Interface Shear Strength Between Implants and Bone," *Clinical Implant Materials, Advances in Biomaterials*, vol. 9, 1990 pp. 309-314.

Patrick J. Henry, B.D.Sc., M.S.D., F.R.A.C.D.S., "Comparative Surface Analysis of Two Osseointegrated Implant Systems" (Ref. D19), 1987.

"Influence of Surface Characteristics on Bone Integration of Titanium Implants," *Journal of Biomedical Materials Research*, vol. 25, pp. 889-902, John Wiley & Sons, Inc., 1991.

"Ion-Beam-Sputter Modification of th, e Surface Morphology of Biological Implants," *J.Vac. Soc. Technol.*, vol. 14, No. 1, Jan./Feb. 1977, pp. 326-331.

Journal of Materials Science Materials In Medicine (1997), pp. 721-729 "Bone response to surface modified titanium implants—studies on the tissue response after 1 year to machined and electropolished implants with different oxide thicknesses".

Karagianes, M. T., D.V.M., "*Porous Metals As A Hard Tissue Substitute*," Biomat. Med. Dev., Art. Org., vol. 1, No. 1, pp. 171-181 (1973).

Kasemo, B., et al., "*Metal Selection And Surface Characteristics*," Tissue-Integrated Prostheses Osseointegration In Clinical Dentistry (Quintessence Books), pp. 99-116 (1985).

Kiesweiter et al., "Surface Roughness Modulates the Local Production of Growth Factors and Cytokines by Osteoblast-Like MG-63 Cells," *Journal of Biomedical Materials Research*, vol. 32, (1996), pp. 55-63.

Klokkevold, P., et al., "*Evaluation Of A New Chemically Enhanced Implant Surface By Torque Removal Tests In The Rabbit Femur*," Clinical Oral Implants Research (1997).

Lazzara, R., et al., "*Retrospective Multicenter Analysis Of 31 Endosseous Dental Implants Placed Over A Five Year Period*," Clinical Oral Implants Research, vol. 7, pp. 73-83 (1996).

Philippe D. Ledermann, Dr. med. dent., "Die Quintessenz" (Ref. 26), 1988.

Ledermann et al., *The Ha-TI Implant*, Schweiz Monatsschr Zahnmed, vol. 101:May 1991 (7 pages).

Philippe D. Ledermann, Dr. med. dent. "Heute so zuverlässig wie vor 50 Jahren" German (Ref. D4), 1988.

Philippe D. Ledermann, Dr. med. dent., "Swiss Dent" (Ref. D25), 1988.

Dana C. Mears, B.M., B.Ch., Ph.D., M.R.C.P., F.R.C.S. (C), "Materials and Orthopaedic Surgery" (Ref. 42), 1979.

Messersmith, P., et al., "*Stress Enhancement And Fatigue Susceptibility Of Porous Coated Ti-6A1-4V Implants: An Elastic Analysis*," Journal of Biomedical Materials Research, vol. 24, pp. 591-604 (1990).

Microfocus (Ref. D50), 1996.

W. M. Murphy, "Tissue Reaction of Rats and Guinea-Pigs to Co-Cr Implants With Different Surface Finishes" (Ref. D8), 1970.

Olefjord, Ingemar, et al., "*Surface Analysis Of Four Dental Implant Systems*," International Journal of Oral & Maxillofacial Implants, vol. 8, No. 1, pp. 32-40 (1993).

Orale Implantologie (Ref. 36), 1988.

Paragon Technology Report (Oct. 1997).

Persson LG, Berglundh T, Sennerby L, Lindhe J., "Re-Osseointegration After Treatment of Peri-Implantitis at Different Implant Surfaces. An Experimental Study in the Dog," *Clin Oral Impl. Res.*, 12 (2001), pp. 595-603.

Predecki, Paul, et al., "*Attachment Of Bone To Threaded Implants By Ingrowth And Mechanical Interlocking*," Journal of Biomedical Materials Research, vol. 6, pp. 401-412 (1972).

Price List, Friatec, 40 pages (Oct. 1998).
Price List and Catalog, Friadent, 35 pages (Sep. 2000).
Product Literature for Frialit®-2, Abridged Directions For Use, Interpore International and Friatec, 20 pages (believed to be 1996 or 1997).
Product Literatyre for Frialit®-2, Friadent, 2 pages (believed to be 2000).
Product Literature for Frialit®-2 Implant System, Friadent, 12 pages (Feb. 1999).
Product Literature for Frialit®-2 Implant System, Interpore International and Friatec, 3 pages (1996).
Removal Torques for Polished and Rough Titanium Implants (Ref. D49), 1988.
W. Eugene Roberts, D.C.S., Ph.D., et al., "Osseous adaptation to continuous loading of rigid endosseous implants" (Ref. D7), 1984.
"Short-term Plasma-cleaning Treatments Enhance In Vitro Osteoblast Attachment to Titanium," *Journal of Oral Implantology*, vol. XVIII, No. 2 (1992), pp. 130-137.
Schulte, J., "*External Hex Manufacturing Tolerances Of Six Implant Systems: A Pilot Study*," Implant Dentistry, pp. 51-53 (Spring 1994).
Schulte, W., et al., "The First 15 Years Of The Tuebinger Implant And Its Further Development To The Frialit®-2 System," Zeitschrift für Zahnärztliche Implantologie, Band VIII, cover page, pp. 3-22 (Feb. 1992).
Schwartz et al., "Effect of Titanium Surface Roughness on Chonrocyte Proliferation, Matrix Production, and Differentiation Depends on the State of Cell Maturation," *Journal of Biomedical Materials Research*, vol. 30, 145-155 (1996), pp. 145-155.
Shultz, R. R., et al., "*A Study Of Fatigue Properties Of Hydroxylapatite Coated Titanium Alloy Implant Materials*," Department of Biomedical Engineering, Memphis State University, 1997.
Smith, Todd, "The Effect of Plasma-Sprayed Coatings on the Fatigue of Titanium Alloy Implants" (Ref. 29), 1994.
Sorensen, J., et al., "*Comparison Of Interface Fidelity Of Implant Systems*," Journal of Dental Research, vol. 70, No. 540, Abstract No. 2191 (1991).
Standard Practice for Surface Preparation and Marking of Metallic Surgical Implants (Ref. D5), 1987.
Standard Recommended Practice for Descaling and Cleaning Titanium and Titanium Alloy Surfaces (Ref. D6), 1985.
David E. Steflik, MS, EdD, et al., "Histomorphometry of the Dental Implant-Bone Interface: One-Year Results of a Comparative Invesitgation in Dogs", pp. 501-511, 1994.
David E. Steflik, MS, EdD, et al., "A Comparative Investigation in Dogs: 2-Year Morphometric Results of the Dental Implant-Bone Interface", pp. 15-25, 1996.
"Step-Screw Implant," *Dental Products Report*, Mar. 1993.
Strauman SLA: Reducing healing time further.
Strauman Literature Abstracts.
Sullivan, Daniel, et al., "*Preliminary Results Of A Multicenter Study Evaluating Chemically-Enhanced Pure Titanium Implants*," Journal of Prosthetic Dentistry (1997).
Sutter et al., *The New Restorative Cocnept of the ITI Dental Implant System: Design and Engineering*; vol. 13, No. 5, pp. 408-413, 1993.

S.A.V. Swanson, DSc (Eng), PhD, DIC, ACGI, MIMechE, et al. "The Scientific Basis of Joint Replacement" (Ref. D41), 1977.
Tarnow, Dennis P., DDS, "*Dental Implants In Periodontal Care*," Current Science, 1993, pp. 157-162.
The Dependence of the Removal Torque of a Leg Screw Surface and Implantation Time (Ref. D30), 1976.
"The Influence Of Implant Surface On Hard- And Soft Tissue Integration," Friatec website, 11 pages (written after Jun. 6, 1998).
"The Influence of Various Titanium Surfaces On the Interface Strength between Implants and Bone," *Advances in Biomaterials*, vol. 9, pp. 309-314, Elsevier Science Publishers BV, Amsterdam, 1990.
Kevin A. Thomas et al., "An evaluation of variables influencing implant fixation by direct bone appostion" (Ref. 46), 1985.
Thomas, K. A., et al., "*The Effect Of Surface Macrotexture And Hydroxylapatite Coating On The Mechanical Strengths And Histologic Profiles Of Titanium Implant Materials*," Journal of Biomedical Materials Research, vol. 21, pp. 1395-1414 (1987).
Titan (Ref. D35), 1951.
University of Bern (Switzerland), Clinic for Dental Maintenance (Schweizerisch Monatschrift für Zahnheilkunde, vol. 86, No. 7, Jul. 1976, pp. 713-727).
Weinlaender, M., et al., "*Histomorphometry Of Bone Apposition Around Three Types Of Endosseous Dental Implants*," International Journal of Oral & Maxillofacial Implants, vol. 7, No. 4, pp. 491-496 (1992).
Wennerberg, A., et al., "*Design And Surface Characteristics Of 13 Commercially Available Oral Implant Systems*," International Journal of Oral & Maxillofacial Implants, vol. 8, No. 6, pp. 622-633 (1993).
Wheeler, K. R., et al., "*Porous Metals As A Hard Tissue Substitute. Part II. Porous Metal Properties*," Biomat. Med. Dev., Art. Org., vol. 1, No. 2, pp. 337-348 (1973).
Wheeler, Stephen L., "*Eight Year Clinical Retrospective Study Of Titanium Plasma-Sprayed And Hydroxyapatite-Coated Cylinder Implants*," International Journal of Oral & Maxillofacial Implants, vol. 11, No. 3, pp. 340-350 (1996).
Wilke, H. J., et al., "*The Influence Of Various Titanium Surfaces On The Interface Shear Strength Between Implants And Bone*," Advances in Biomaterials, Elsevier Science Publishers B.V., Amsterdam, vol. 9, pp. 309-314 (1990).
Wong, M., et al., "*Effect Of Surface Topology On The Osseointegration Of Implant Materials In Trabecular Bone*," Journal of Biomedical Materials Research, vol. 29, pp. 1567-1575 (1995).
Yue, S., et al., "*The Fatigue Strength Of Porous-Coated Ti-6%Al-4%V Implant Alloy*," Journal of Biomedical Materials Research, vol. 18, pp. 1043-1058 (1984).
Decision on Appeal from the U.S. Patent & Trademark Office in U.S. Appl. No. 09/237,605 dated May 30, 2007.
Request for Rehearing of Decision on Appeal filed by Applicant in U.S. Appl. No. 09/237,605 dated Jul. 30, 2007.
Decision on Request for Rehearing in U.S. Appl. No. 09/237,605 dated Nov. 13, 2007.

IMPLANT SURFACE PREPARATION

CROSS REFERENCE TO RELATED APPLICATION

This application is a continuation of U.S. application Ser. No. 11/651,115 filed Jan. 9, 2007; which is a continuation of U.S. application Ser. No. 11/172,775 filed Jul. 1, 2005 now U.S. Pat. No. 7,169,317; which is a continuation of U.S. application Ser. No. 10/701,855 filed Nov. 5, 2003 (issued as U.S. Pat. No. 6,969,474); which is a continuation of U.S. application Ser. No. 09/777,335 filed Feb. 6, 2001 (issued as U.S. Pat. No. 6,652,765); which is a continuation of U.S. patent application Ser. No. 09/259,432 filed Mar. 1, 1999 (issued as U.S. Pat. No. 6,491,723), which is a continuation of U.S. patent application Ser. No. 08/607,903, filed Feb. 27, 1996 (issued as U.S. Pat. No. 5,876,453), which claims priority of PCT/US95/15576, filed on Nov. 30, 1995, and which is a continuation-in-part of U.S. patent application Ser. No. 08/351,214, filed Nov. 30, 1994, (now abandoned) for "Implant Surface Preparation."

FIELD OF THE INVENTION

The present invention relates to processes for improving the surfaces of devices to be surgically implanted in living bone, and to implant devices having the improved surfaces.

BACKGROUND OF THE INVENTION

The success of prosthetic devices surgically implanted in living bone depends substantially entirely on achieving and maintaining an enduring bond between the confronting surfaces of the device and the host bone. Surgical procedures for preparing living bone to receive a surgically implanted prosthetic device have been known for twenty years or more, but considerable controversy remains concerning the ideal properties of the surface of the device which confronts the host bone.

It is known through clinical experience extending over several decades that titanium and its dilute alloys have the requisite biocompatibility with living bone to be acceptable materials for use in making surgically implantable prosthetic devices, when the site of installation is properly prepared to receive them. There is, however, less certainty about the ideal physical properties of the surfaces of the prosthetic devices which confront the host bone. For example, the endosseous dental implant made of titanium enjoys sufficient predictable success to have become the artificial root most frequently chosen for restoring dentition to edentulous patients, but that success depends in part on the micromorphologic nature of the surface of the implant which comes in contact with the host bone. Because there is no standard for the surface micromorphology of dental implants, the surfaces of commercial implants have a wide range of available textures. It is known that osseointegration of dental implants is dependent, in part, on the attachment and spreading of osteoblast-like cells on the implant surface. It appears that such cells will attach more readily to rough surfaces than to smooth surfaces, but an optimum surface for long-term stability has not yet been defined.

Wilke, H. J. et al. have demonstrated that it is possible to influence the holding power of implants by altering surface structure morphology: "The Influence of Various Titanium Surfaces on the Interface Strength between Implants and Bone", *Advances in Biomaterials*, Vol. 9, pp. 309-314, Elsevier Science Publishers BV, Amsterdam, 1990. While showing that increased surface roughness appeared to provide stronger anchoring, these authors comment that it "cannot be inferred exclusively from the roughness of a surface as shown in this experiment. Obviously the shear strength is also dependent on the kind of roughness and local dimensions in the rough surface which can be modified by chemical treatment."

Buser, D. et al., "Influence of Surface Characteristics on Bone Integration of Titanium Implants", *Journal of Biomedical Materials Research*, Vol. 25, pp. 889-902, John Wiley & Sons, Inc., 1991, reports the examination of bone reactions to titanium implants with various surface characteristics to extend the biomechanical results reported by Wilke et al. The authors state that smooth and titanium plasma sprayed ("TPS") implant surfaces were compared to implant surfaces produced by alternative techniques such as sandblasting, sandblasting combined with acid treatment, and plasma-coating with HA. The evaluation was performed with histomorphometric analyses measuring the extent of the bone-implant interface in cancellous bone. The authors state, "It can be concluded that the extent of bone-implant interface is positively correlated with an increasing roughness of the implant surface."

Prior processes that have been used in attempts to achieve biocompatible surfaces on surgically implantable prosthetic devices have taken many forms, including acid etching, ion etching, chemical milling, laser etching, and spark erosion, as well as coating, cladding and plating the surface with various materials, for example, bone-compatible apatite materials such as hydroxyapatite or whitlockite or bone-derived materials. Examples of U.S. patents in this area are U.S. Pat. No. 3,855,638 issued to Robert M. Pilliar Dec. 24, 1974 and U.S. Pat. No. 4,818,559 issued to Hama et al. Apr. 04, 1989. A process of ion-beam sputter modification of the surface of biological implants is described by Weigand, A. J. et al. in *J. Vac. Soc. Technol.*, Vol. 14, No. 1, Jan./Feb. 1977, pp. 326-331.

As Buser et al. point out (Ibid p. 890), the percentage of bone-implant contact necessary to create sufficient anchorage to permit successful implant function as a load-bearing device over time remains unclear. Likewise, Wennerberg et al., "Design and Surface Characteristics of 13 Commercially Available Oral Implant Systems", *Int. J. Oral Maxillofacial Implants* 1993, 8:622-633, show that the different implants studied varied considerably in surface topography, and comment: "Which of the surface roughness parameters that will best describe and predict the outcome of an implant is not known" (p. 632).

Radio-frequency glow-discharge treatment, also referred to as plasma-cleaning ("PC") treatment, is discussed in Swart, K. M. et al., "Short-term Plasma-cleaning Treatments Enhance in vitro Osteoblast Attachment to Titanium", *Journal of Oral Implantology*, Vol. XVIII, No. 2 (1992), pp. 130-137. These authors comment that gas plasmas may be used to strip away organic contaminants and thin existing oxides. Their conclusions suggest that short-term PC treatments may produce a relatively contaminant-free, highly wettable surface. U.S. Pat. Nos. 5,071,351, issued Dec. 10, 1991, and 5,188,800, issued Feb. 23, 1993, both owned by the assignee of the present application, describe and claim methods and means for PC cleaning of a surgical implant to provide a contact angle of less than 20 degrees.

Copending application Ser. No. 08/149,905, filed Nov. 10, 1993, owned by the assignee of the present application, describes and claims inventions for improving the surfaces of surgically implantable devices which employ, among other features, impacting the surface with particles of the same material as the device to form the surface into a desired pattern of roughness.

SUMMARY OF THE INVENTION

It is a primary object of the present invention to produce an implant surface having a roughness that is substantially uniform over the area of the implant that is intended to bond to the bone in which the implant is placed.

It is a further object of this invention to provide an improved surgically implantable device having on its surface a substantially uniform micromorphology.

It is another object of the invention to provide a process or processes for manufacturing such improved implant devices.

It is an additional object of the invention to provide such improved implant devices which can be manufactured without contaminating the surfaces thereof.

It is a more specific object of the invention to provide an improved etch-solution process that will result in a substantially uniform surface topography on surgically implantable devices.

In accordance with the present invention, the foregoing objectives are realized by removing the native oxide layer from the surface of a titanium implant to provide a surface that can be further treated to produce a substantially uniform surface texture or roughness, and then performing a further, and different, treatment of the resulting surface substantially in the absence of unreacted oxygen. The removal of the native oxide layer may be effected by any desired technique, but is preferably effected by immersing the implant in hydrofluoric acid under conditions which remove the native oxide quickly while maintaining a substantially uniform surface on the implant. The further treatment is different from the treatment used to remove the native oxide layer and produces a desired uniform surface texture, preferably acid etching the surface remaining after removal of the native oxide layer. To enhance the bonding of the implant to the bone in which it is implanted, a bone-growth-enhancing material, such as bone minerals, hydroxyapatite, whitlockite, or bone morphogenic proteins, may be deposited on the treated surface. The implant is preferably maintained in an oxygen-free environment following removal of the native oxide layer, in order to minimize the opportunity for oxide to re-form before the subsequent treatment is performed.

DETAILED DESCRIPTION OF THE PREFERRED EMBODIMENTS

Figure 1:
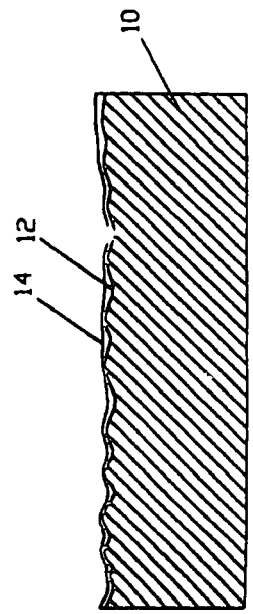
FIG. 1 is a diagrammatic sectional view taken through a body of titanium covered with a layer of native oxide.

Turning now to the drawings, and referring first to FIG. 1, a titanium body 10 which has been exposed to air has on its outer surface 12 an irregular layer 14 of an oxide or oxides of titanium which form naturally. This oxide layer 14 is referred to herein as the "native oxide" layer, and typically has a thickness in the range from about 70 to about 150 Angstroms. The native oxide layer that forms naturally on titanium when it is exposed to air is actually a combination of different oxides of titanium, including TiO, $TiO_2$, $Ti_2O_3$ and $Ti_3O_4$. The concentration of these oxides in the titanium body diminishes with distance from the surface of the body. The oxide concentration may be measured in an Auger spectrometer.

Auger electron spectroscopy (AES) measures the energy of Auger electrons produced when an excited atom relaxes by a radiationless process after ionization by a high energy electron, ion or x-ray beam. The spectra of a quantity of electrons emitted as a function of their energy reveal information about the chemical environment of the tested material. One of the major uses of AES is the depth profiling of materials, to reveal the thickness (depth) of the oxide layer on the surfaces of materials. These Auger electrons lie in an energy level that extends generally between the low energy level of the emission of secondary electrons up to the energy of the impinging electron beam. In this region, small peaks will occur in the spectra at certain energy levels that identify the existence of certain elements in the surface.

Figure 7:
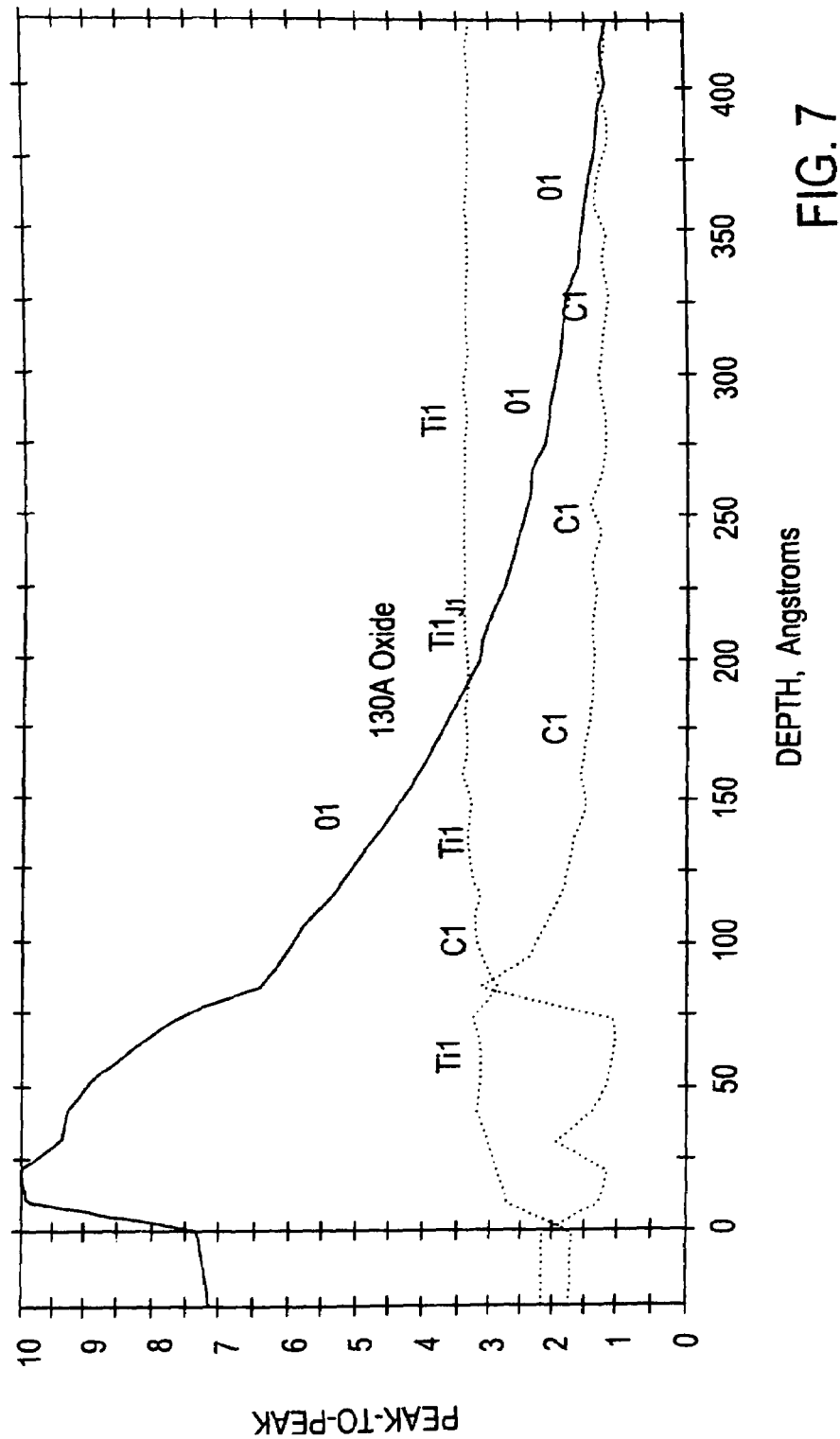
FIG. 7 is a graph of the results of an Auger electron spectroscopic analysis of a titanium surface that has been exposed to air.
Figure 8A:
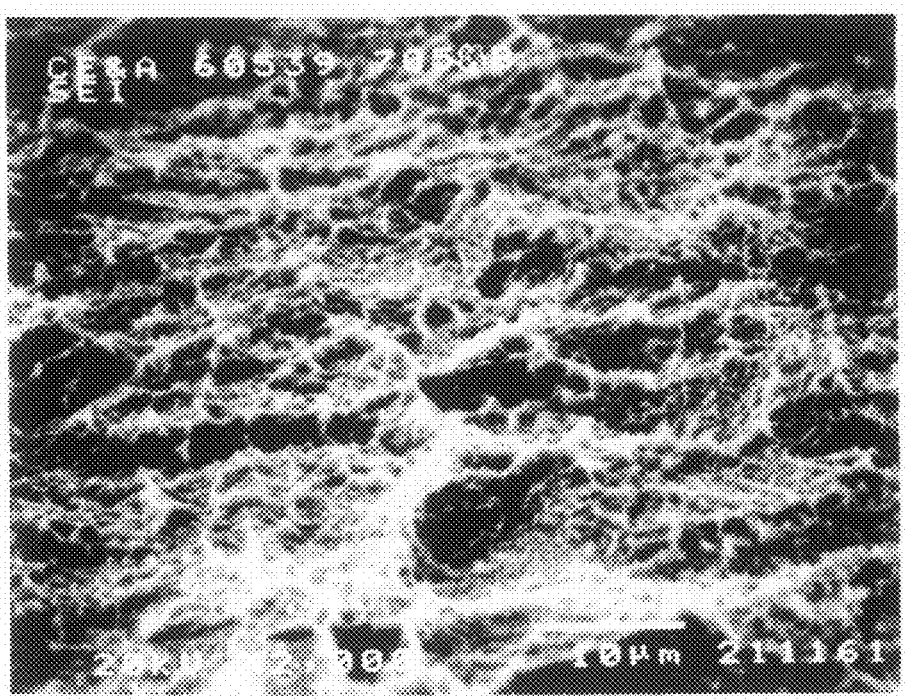
FIGS. 8A and 8B are SEMs of two titanium dental implants prepared in accordance with the present invention.
Figure 8B:
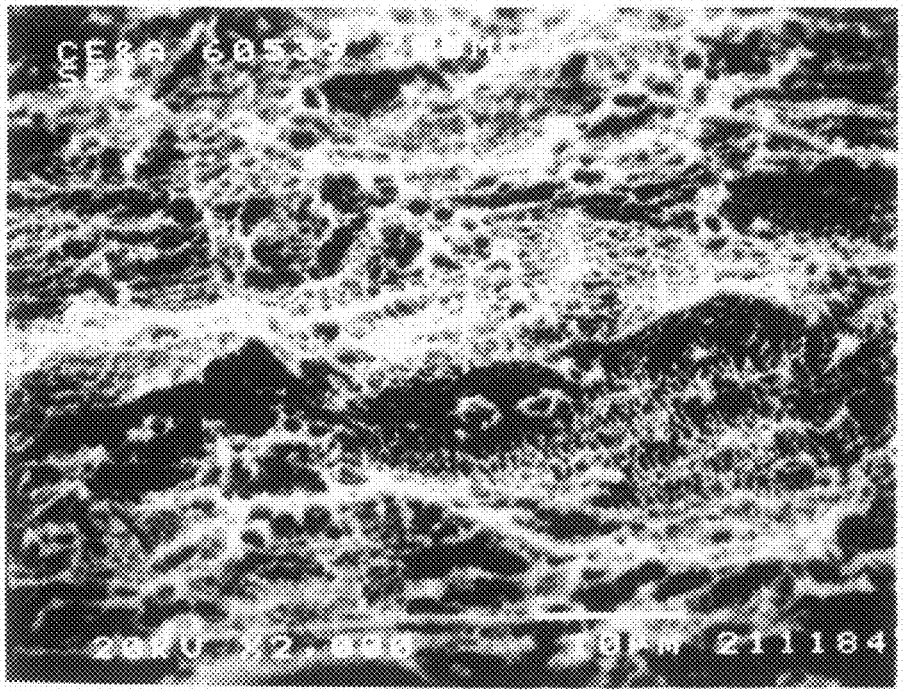
Figure 9A:
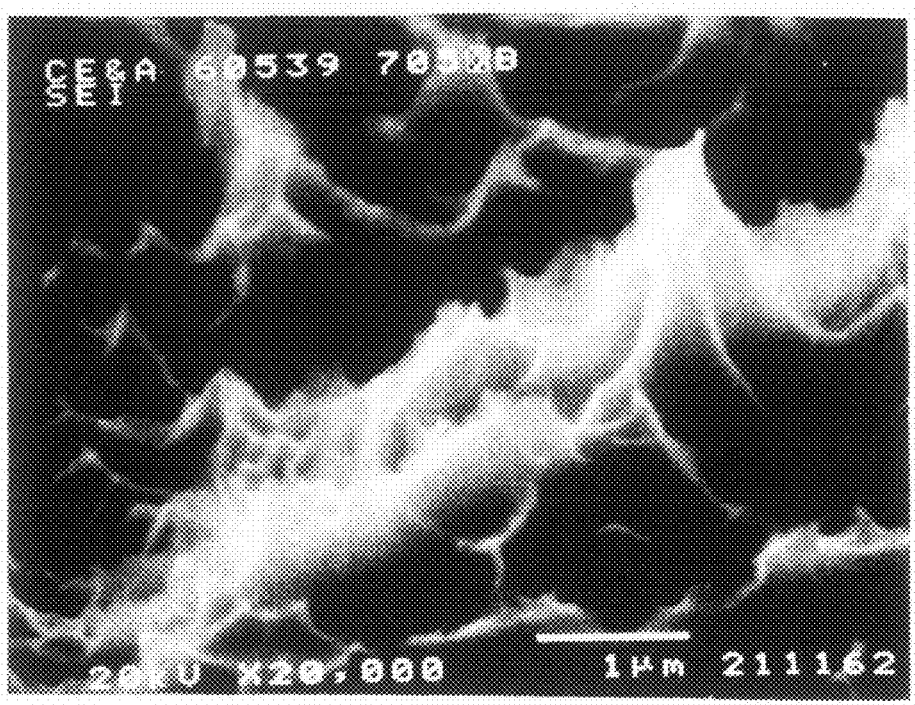
FIGS. 9A and 9B are SEMs of the same implants shown in FIGS. 8A and 8B, at a higher magnification level.
Figure 9B:
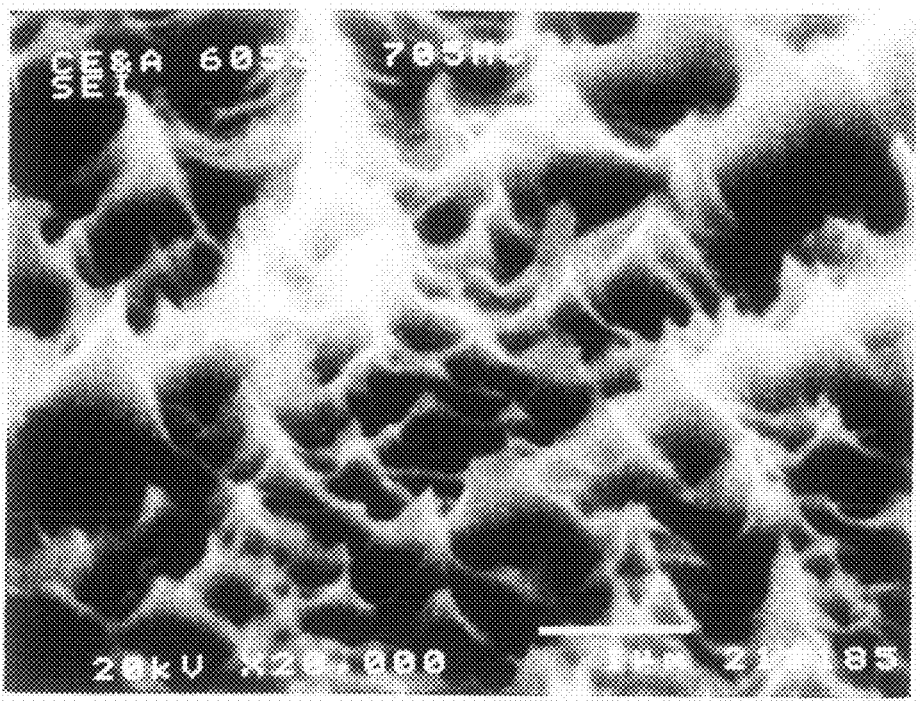

As used herein, the term "native oxide layer" refers to the layer which extends from the surface of the material to the depth at which the energy of the peak-to-peak oxygen profile as measured in an Auger electron spectrometer decreases by one-half. For example, in the peak-to-peak oxygen profile reproduced in FIG. 7, the thickness of the native oxide layer was 130 Angstroms, which is the depth at which the oxygen profile dropped to half its maximum intensity. Thus, removal of a 130-Angstrom layer from the surface of the titanium body would remove the native oxide layer.

Figure 2:
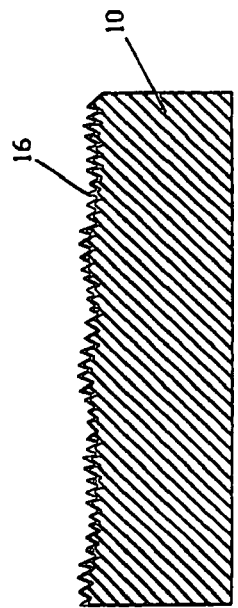
FIG. 2 is the same section shown in FIG. 1 after impacting the surface with a grit.

FIG. 2 depicts the surface 12 of the titanium body 10 after being grit blasted to achieve initial roughening, as described in more detail below. The oxide layer 14 is still present, but it has a rougher surface than in its original state depicted in FIG. 1.

Figure 3:
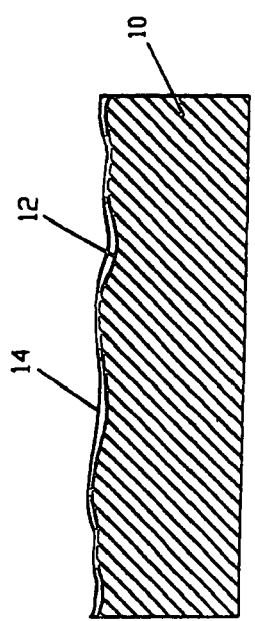
FIG. 3 is the same section shown in FIG. 2 after bulk etching with an acid etch.

FIG. 3 depicts the grit-blasted surface 12 of the titanium body 10 after it has been bulk etched in an etching acid. The etched area 16 where the native oxide layer 14 has been removed by the etching acid exhibits a much finer roughness, but in areas where the oxide layer remains, the initial roughness depicted in FIG. 2 also remains.

Figure 4:
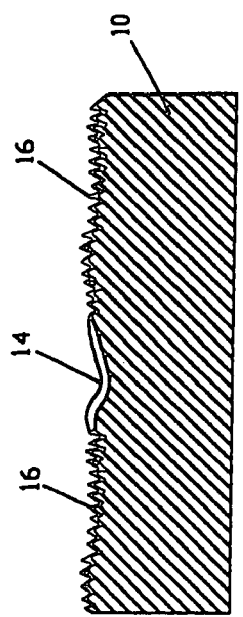
FIG. 4 is the same section shown in FIG. 2 after first removing the native oxide and then bulk etching with an acid.
Figure 5A:
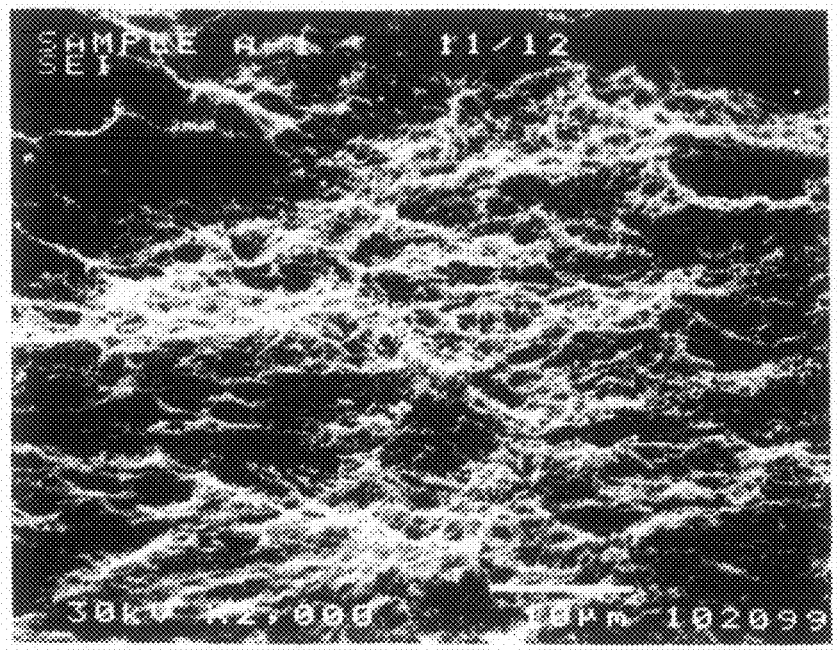
FIGS. 5A and 5B are scanning electron micrographs ("SEMs") of two titanium dental implants prepared in accordance with the present invention.
Figure 5B:
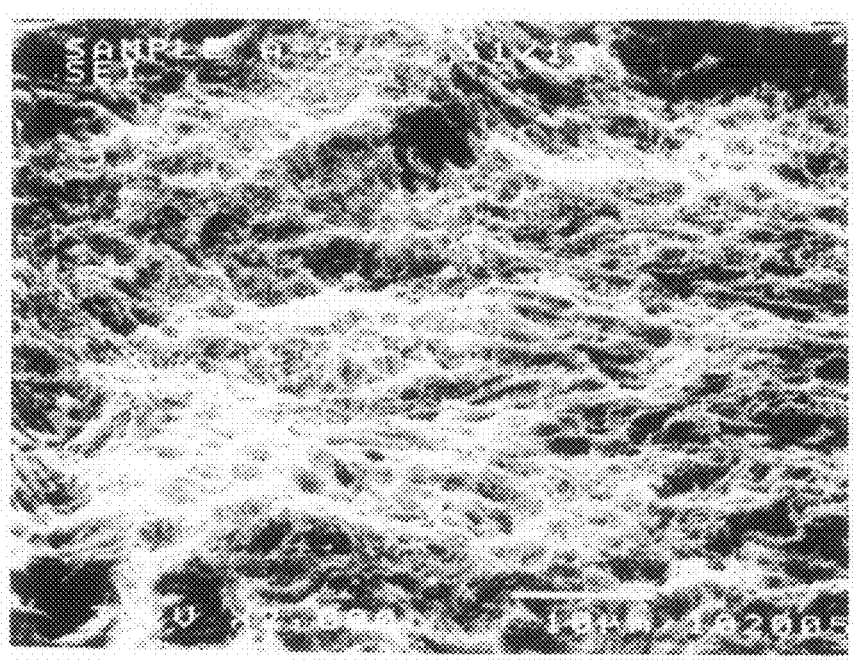
Figure 6A:
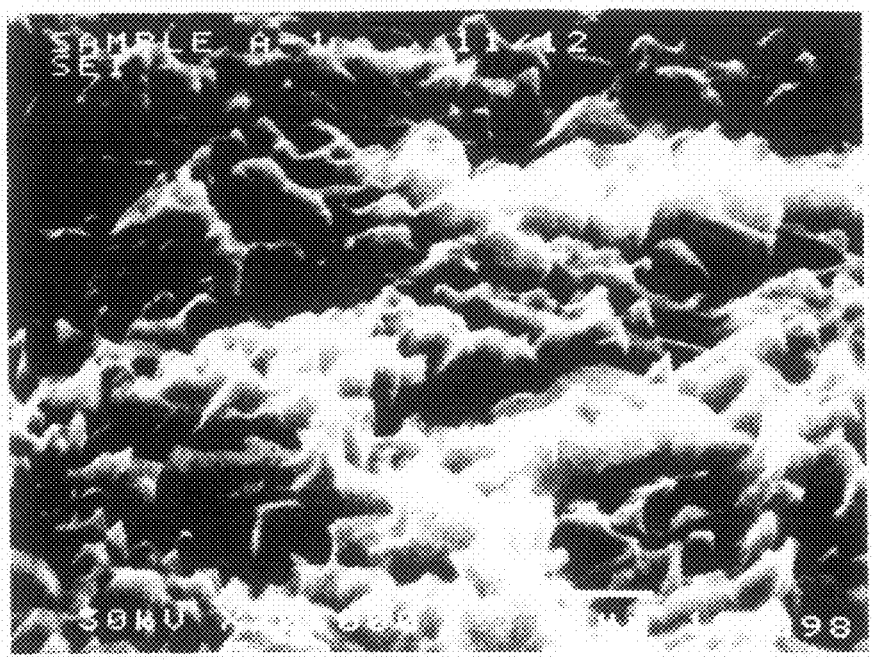
FIGS. 6A and 6B are SEMs of the same implants shown in FIGS. 5A and 5B, at a higher magnification level.
Figure 6B:
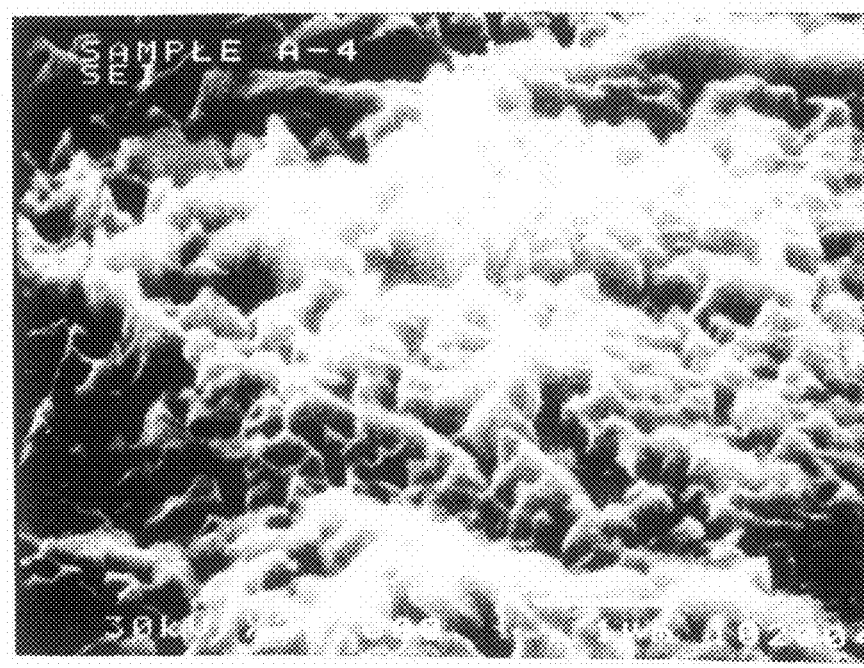

FIG. 4 depicts the grit-blasted surface 12 of the titanium body 10 after it has been etched in a first acid to remove the native oxide layer 14, and then in a second acid to produce the desired topography on the surface 16 produced by the first acid treatment. As described in more detail below, the preferred surface topography has a substantially uniform, fine roughness over the entire surface 16.

Among the processes previously used to improve the surfaces of dental implants made of titanium is that of etching the surface with an acid, such as a mixture of two parts (by volume) sulfuric acid and one part (by volume) muriatic acid. It has been found that such acid treatments do not etch an oxidized implant surface uniformly or consistently from one region to another.

According to one aspect of the present invention, the native oxide layer is removed from the surface of a titanium implant prior to the final treatment of the surface to achieve the desired topography. After the native oxide layer is removed, a further and different treatment of the surface is carried out in the absence of unreacted oxygen to prevent the oxide layer from re-forming until after the desired surface topography has been achieved. It has been found that this process permits the production of unique surface conditions that are substantially uniform over the implant surface that is so treated.

Removal of the native oxide layer can be effected by immersing the titanium implant in an aqueous solution of hydrofluoric (HF) acid at room temperature to etch the native oxide at a rate of at least about 100 Angstroms per minute. A preferred concentration for the hydrofluoric acid used in this oxide removal step is 15% $HF/H_2O$. This concentration produces an etch rate of approximately 200-350 Angstroms per minute at room temperature, without agitation, so that a typical native oxide layer having a thickness in the range from about 70 to about 150 Angstroms can be removed in about one-half minute. Other suitable etching solutions for removing the native oxide layer, and their respective etch rates, are:

50% HF–etch rate~600 to 750 Angstroms/min.
30% HF–etch rate~400 to 550 Angstroms/min.
10% HF–etch rate~100 to 250 Angstroms/min.

A 100% HF was found to be difficult to control, and the etch rate was not determined. The preferred 15% HF solution allows substantially complete removal of the native oxide layer with minimum further consumption of the titanium surface after the implant is removed from the solution.

The native oxide layer may be removed by the use of other acids, or by the use of techniques other than acid etching. For example, the Swart et al. article cited above mentions the use of plasma cleaning to remove thin oxides. Regardless of what technique is used, however, it is important to remove substantially all the native oxide from the implant surface that is intended to interface with the living bone, so that the subsequent treatment of that surface produces a substantially uniform surface texture to promote uniform bonding to the living bone. The native oxide layer is preferably removed from substantially the entire bone-interfacing surface of the implant. In the case of screw-type dental implants, the bone-interfacing surface typically includes the entire implant surface beyond a narrow collar region on the side wall of the implant at the gingival end thereof. This narrow collar region preferably includes the first turn of the threaded portion of the implant. It is preferred not to etch the gingival end itself, as well as the narrow collar region, because these portions of the implant are normally fabricated with precise dimensions to match abutting components which are eventually attached to the gingival end or the implant. Moreover, it is preferred to have a smooth surface on that portion of a dental implant that is not embedded in the bone, to minimize the risk of infection.

The treatment that follows removal of the native oxide layer must be different from the treatment that is used to remove the native oxide layer. A relatively aggressive treatment is normally required to remove the oxide layer, and such an aggressive treatment does not produce the desired uniform surface texture in the resulting oxide-free surface. Thus, after the native oxide layer has been removed, the resulting implant surface is immediately rinsed and neutralized to prevent any further attack on the implant surface. The surface is then subjected to the further, and different, treatment to produce a desired uniform surface texture. For example, the preferred further treatment described below is a relatively mild acid-etching treatment which forms a multitude of fine cone-like structures having relatively uniform, small dimensions. Because of the prior removal of the native oxide layer, even a mild second treatment of the implant surface can produce a substantially uniform effect over substantially the entire bone-interfacing surface of the implant.

Prior to removing the native oxide layer, the oxide-bearing surface may be grit blasted, preferably with grit made of titanium or a dilute titanium alloy. As is taught in the aforementioned copending U.S. patent application Ser. No. 08/149,905, the use of a grit made of titanium avoids contaminating the surface of a titanium implant. Thus, for a dental implant made of commercially pure ("CP") titanium, the blasting material may be CP B299 SL grade titanium grit. The preferred particle size for this grit is in the range from about 10 to about 60 microns (sifted), and the preferred pressure is in the range from about 50 to about 80 psi.

The surface treatment that follows removal of the native oxide layer from the implant surface may take several forms, singly or in combination. The preferred treatment is a second acid etching step, using an etch solution ("Modified Muriaticetch") consisting of a mixture of two parts by volume sulfuric acid (96% by weight $H_2SO_4$, 4% by weight water) and one part by volume hydrochloric acid (37% by weight HCl, 63% by weight water) at a temperature substantially above room temperature and substantially below the boiling point of the solution, preferably in the range from about 60° C. to about 80° C. This mixture provides a sulfuric acid/hydrochloric acid ratio of about 6:1. This preferred etch solution is controllable, allowing the use of bulk etch times in the range from about 3 to about 10 minutes. This solution also can be prepared without the risk of violent reactions that may result from mixing more concentrated HCl solutions (e.g., 98%) with sulfuric acid. This second etching treatment is preferably carried out in the absence of unreacted oxygen, and before the implant surface has been allowed to re-oxidize, following removal of the native oxide layer. Of course, the implants may be kept in an inert atmosphere or other inert environment between the two etching steps.

The second etching step produces a surface topography that includes many fine projections having a cone-like aspect in the sub-micron size range. Because of the fine roughness of the surface, and the high degree of uniformity of that roughness over the treated surface, the surface topography produced by this process is well suited for osseointegration with adjacent bone. As illustrated by the working examples described below, the final etched surface consists of a substantially uniform array of irregularities having peak-to-valley heights of less than about 10 microns. Substantial numbers of the irregularities are substantially cone-shaped elements having base-to-peak heights in the range from about 0.3 microns to about 1.5 microns. The bases of these cone-shaped elements are substantially round with diameters in the range from about 0.3 microns to about 1.2 microns, and spaced from each other by about 0.3 microns to about 0.75 microns. The SEMs discussed below, and reproduced in the drawings, illustrate the surface topography in more detail.

The acid-etched surface described above also provides a good site for the application of various materials that can promote bonding of the surface to adjacent bone. Examples of such materials are bone-growth-enhancing materials such as bone minerals, bone morphogenic proteins, hydroxyapatite, whitlockite, and medicaments. These materials are preferably applied to the etched surface in the form of fine particles which become entrapped on and between the small cone-like structures. The bone-growth-enhancing materials are preferably applied in the absence of oxygen, e.g., using an inert atmosphere.

The roughness of the surface to which these materials are applied enhances the adherence of the applied material to the titanium implant. The uniformity of the rough surface enhances the uniformity of the distribution of the applied material, particularly when the material is applied as small discrete particles or as a very thin film.

A preferred natural bone mineral material for application to the etched surface is the mineral that is commercially available under the registered trademark "BIO-OSS". This material is a natural bone mineral obtained from bovine bone; it is described as chemically comparable to mineralized human bone with a fine, crystalline biological structure, and able to support osseointegration of titanium fixtures.

The invention will be further understood by reference to the following examples, which are intended to be illustrative and not limiting:

EXAMPLE NO. 1

A batch of 30 screw-type cylindrical implants made of CP titanium were grit blasted using particles of CP B299 SL grade titanium grit having particle sizes ranging from 10 to 45 microns, at a pressure of 60 to 80 psi. After grit-blasting, native oxide layer was removed from the implant surfaces by placing 4 implants in 100 ml. of a 15% solution of HF in water at room temperature for 30 seconds. The implants were then removed from the acid, neutralized in a solution of baking soda, and placed in 150 ml. of "Modified Muriaticetch" (described above) at room temperature for 3 minutes. The implants were then removed from the acid, neutralized, rinsed and cleaned. All samples displayed very similar surface topographies and a high level of etch uniformity over the surface, when compared with each other in SEM evaluations. Consistency in the surface features (peaks and valleys) was also observed. The SEMs in FIGS. 5A, 5B, 6A and 6B show the surfaces of two of the implants, Sample A-1 and Sample A-4, at magnifications of 2,000 and 20,000. It will be observed that the surface features over the areas shown are consistent and uniform. The scale shown on the ×20,000 photographs is 1 micron=0.564 inch. At this magnification the surfaces appear to be characterized by a two-dimensional array of cones ranging in height (as seen in the SEMs) from about 0.17 inch to about 0.27 inch; the base diameters of these cones varied from about 0.17 inch to about 0.33 inch. Converting these numbers to metric units on the above-mentioned scale (1 micron=0.564 inch) yields:

cone height range (approx.)=0.30 to 0.50 micron
cone base diameter range (approx.)=0.30 to 0.60 micron.

The same degree of uniformity was found in all the samples, and from sample to sample, at magnifications of 2,000 and 20,000, as compared with similar samples subjected to bulk etching without prior removal of the native oxide, as described in EXAMPLE NO. 2 below.

EXAMPLE NO. 2

Four of the implants that had been grit blasted as described in EXAMPLE NO. 1 above were placed in 150 ml. of "Modified Muriaticetch" for 10 minutes. The implants were then removed, neutralized, rinsed and cleaned. SEM photographs taken at magnifications of 2,000 and 20,000 showed that the bulk etch solution failed to remove the native oxide layer after 10 minutes in the etch solution. The failure to remove the native oxide layer (100-150 Angstrom units thick) resulted in a non-uniformly etched surface, as depicted in FIG. 3. In areas of the implant surfaces where the native oxide was removed, the topography was similar to that observed on the implants in EXAMPLE NO. 1.

EXAMPLE NO. 3

The procedure of this example is currently preferred for producing commercial implants. A batch of screw-type implants made of CP titanium were immersed in a 15% solution of HF in water at room temperature for 60 seconds to remove the native oxide layer from the implant surfaces. A plastic cap was placed over the top of each implant to protect it from the acid. The implants were then removed from the acid and rinsed in a baking soda solution for 30 seconds with gentle agitation. The implants were then placed in a second solution of baking soda for 30 seconds, again with agitation of the solution; and then the implants were rinsed in deionized water. Next the implants were immersed in another solution of two parts by volume sulfuric acid (96% by weight $H_2SO_4$, 4% by weight water) and one part by volume hydrochloric acid (37% by weight HCl, 63% by weight water) at 70° C. for 5 minutes. The implants were then removed from the acid and rinsed and neutralized by repeating the same steps carried out upon removal of the implants from the HF. All samples displayed very similar surface topographies and a high level of etch uniformity over the surface, when compared with each other in SEM evaluations. Consistency in the surface features (peaks and valleys) was also observed. The SEMs in FIGS. 8A, 8B, 9A and 9B show the surfaces of two of the implants, Sample 705MB and Sample 705MC, at magnifications of 2,000 and 20,000. It will be observed that the surface features over the areas shown are consistent and uniform. The scale shown on the ×20,000 photographs is 1 micron=0.564 inch. At this magnification the surfaces appear to be characterized by a two-dimensional array of cones ranging in height (as seen in the SEMs) from about 0.17 inch to about 1.128 inch; the base diameters of these cones varied from about 0.17 inch to about 1.128 inch. Converting these numbers to metric units on the above-mentioned scale (1 micron=0.564 inch) yields:

cone height range (approx.)=0.30 to 0.20 microns
cone base diameter range (approx.)=0.30 to 0.20 microns.

The same degree of uniformity was found in all the samples, and from sample to sample, at magnifications of 2,000 and 20,000, as compared with similar samples subjected to bulk etching without prior removal of the native oxide, as described in EXAMPLE NO. 2 above.

The invention claimed is:

1. A method of preparing the surface of an implant to be surgically implanted in living bone and made of titanium, the implant having a surface with a native oxide layer thereon, the method comprising the steps of:
    removing the native oxide layer from the surface;
    acid etching the surface from which the native oxide layer has been removed to form a surface roughness; and
    depositing a layer of hydroxyapatite on the acid-etched surface.

2. The method of claim 1 wherein the depositing occurs in the absence of oxygen.

3. The method of claim 1 wherein the depositing includes adhering, the adhering being enhanced by the roughness of the acid-etched surface.

4. The method of claim 1 wherein the depositing includes applying hydroxyapatite in the form of particles.

5. The method of claim 1 wherein the depositing includes applying hydroxapatite in the form of a film.

6. The method of claim 1 wherein the depositing includes applying hydroxyapatite so as not to disturb the surface from which the native oxide layer has been removed to form a surface roughness.

7. The method of claim 1 wherein the depositing includes applying hydroxyapatite using an inert atmosphere.

8. The method of claim 1 wherein the depositing includes distributing hydroxyapatite, the distributing being enhanced by the surface roughness.

9. The method of claim 1 wherein the removing the native oxide layer is carried out by an acid etching process.

10. The method of claim 1 wherein the surface roughness have peak-to-valley heights less than 10 microns.

11. The method of claim 1 wherein the acid-etching includes producing a surface roughness with an array of irregularities.

12. The method of claim 11 wherein the depositing includes applying hydroxyapatite in the form of fine particles that become entrapped on the irregularities.

13. The method of claim 11 wherein the depositing includes applying hydroxyapatite in the form of particles that become entrapped between the irregularities.

14. The method of claim 11 wherein the irregularities have peak-to-valley heights less than 10 microns.

15. A method of preparing a surface of a device that is surgically implantable in living bone, the device being made of titanium and having a native oxide layer on the surface, the method comprising the steps of:
    removing the native oxide layer from the surface of the device until the depth of the peak-to-peak oxygen profile as measured by Auger spectrometer has decreased to one-half of the initial profile;
    after the removing, performing a roughening treatment on the surface resulting from the removing to produce a roughened surface with an array of irregularities; and
    after the performing a roughening treatment on the surface, depositing a layer of hydroxyapatite on the surface.

16. The method of claim 15 wherein the performing of the roughening treatment includes acid etching.

17. The method of claim 15 wherein the depositing occurs in the absence of oxygen.

18. The method of claim 15 wherein the depositing includes applying hydroxyapatite in the form of particles.

19. The method of claim 15 wherein the depositing includes applying hydroxapatite in the form of a film.

20. The method of claim 15 wherein the removing the native oxide layer is carried out by an acid etching process.

21. The method of claim 15 wherein the irregularities have peak-to-valley heights less than 10 microns.

22. The method of claim 15 wherein the depositing includes applying hydroxyapatite in the form of particles that become entrapped on the irregularities.

23. The method of claim 15 wherein the depositing includes applying hydroxyapatite in the form of particles that become entrapped between the irregularities.

24. The method of claim 15 wherein the depositing includes applying hydroxyapatite in the form of particles that become entrapped on and between the irregularities.

25. A method of preparing the surface of an implant to be surgically implanted in living bone and made of titanium, the implant having a surface with a native oxide layer thereon, the method comprising the steps of:
    removing the native oxide layer from the surface;
    acid etching the surface from which the native oxide layer has been removed to form a surface roughness; and
    depositing a layer of bone growth enhancing material on the acid-etched surface.

26. The method of claim 25 wherein the depositing includes applying the bone growth enhancing material in the form of particles.

27. The method of claim 25 wherein the depositing includes applying the bone growth enhancing material in the form of a film.

28. The method of claim 25 wherein the bone growth enhancing material is hydroxyapatite.

29. The method of claim 25 wherein the removing the native oxide layer is carried out by an acid etching process.

30. The method of claim 25 wherein the surface roughness includes irregularities having peak-to-valley heights less than 10 microns.

31. The method of claim 25 wherein the acid-etching includes producing a surface roughness with an array of irregularities.

32. The method of claim 1, further including the act of grit blasting the surface prior to the act of removing the native oxide layer.

33. The method of claim 32, wherein the act of grit blasting includes using titanium grit.

34. The method of claim 15, further including the act of grit blasting the surface prior to the act of removing the native oxide layer.

35. The method of claim 34, wherein the act of grit blasting includes using titanium grit.

* * * * *